(12) United States Patent
Bourles et al.

(10) Patent No.: US 10,722,470 B2
(45) Date of Patent: Jul. 28, 2020

(54) PHARMACEUTICAL COMPOSITION COMPRISING AN ADENOVIRAL VECTOR

(71) Applicant: GLAXOSMITHKLINE BIOLOGICALS, SA, Rixensart (BE)

(72) Inventors: Erwan Bourles, Rixensart (BE); Frederic Mathot, Rixensart (BE)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 15/746,473

(22) PCT Filed: Jul. 20, 2016

(86) PCT No.: PCT/EP2016/067280
§ 371 (c)(1),
(2) Date: Jan. 22, 2018

(87) PCT Pub. No.: WO2017/013169
PCT Pub. Date: Jan. 26, 2017

(65) Prior Publication Data
US 2018/0214379 A1 Aug. 2, 2018

(30) Foreign Application Priority Data
Jul. 23, 2015 (GB) .................................. 1513010.7

(51) Int. Cl.
| | |
|---|---|
| *A61K 9/19* | (2006.01) |
| *A61K 47/26* | (2006.01) |
| *A61K 39/12* | (2006.01) |
| *A61K 47/02* | (2006.01) |
| *A61K 39/00* | (2006.01) |

(52) U.S. Cl.
CPC ................ *A61K 9/19* (2013.01); *A61K 39/12* (2013.01); *A61K 47/02* (2013.01); *A61K 47/26* (2013.01); *A61K 2039/5256* (2013.01); *C12N 2710/10043* (2013.01); *C12N 2760/14134* (2013.01)

(58) Field of Classification Search
CPC .. A61K 9/19; A61K 2039/5256; A61K 39/12; A61K 48/0091; A61K 47/02; A61K 47/26; C12N 15/86; C12N 2710/10043; C12N 2710/10132; C12N 2710/10143; C12N 2760/14134; A61P 43/00; A61P 37/04
See application file for complete search history.

(56) References Cited

U.S. PATENT DOCUMENTS

| | | | | |
|---|---|---|---|---|
| 2002/0031527 A1* | 3/2002 | Wu | ........................ | A01N 1/02 424/233.1 |
| 2002/0182723 A1 | 12/2002 | Zhang et al. | | |
| 2012/0141528 A1* | 6/2012 | Coffey | ................ | A61K 35/765 424/215.1 |
| 2012/0328651 A1* | 12/2012 | Colloca | ................ | C07K 14/005 424/202.1 |
| 2013/0164296 A1 | 6/2013 | Drew et al. | | |
| 2014/0073032 A1 | 3/2014 | Custers et al. | | |
| 2019/0365930 A1* | 12/2019 | Bourles | ................... | A61P 31/04 |

FOREIGN PATENT DOCUMENTS

| | | | |
|---|---|---|---|
| CN | 1883707 A | 12/2006 | |
| WO | 2007062040 A1 | 5/2007 | |
| WO | 2011121301 A1 | 10/2011 | |
| WO | 2012075376 A2 | 6/2012 | |
| WO | 2013135615 A1 | 9/2013 | |
| WO | WO-2015040234 A1 * | 3/2015 | ........... A61K 9/0019 |

OTHER PUBLICATIONS

Nail SL, Jiang S, Chongprasert S, Knopp SA. Fundamentals of freeze-drying. Pharm Biotechnol. 2002;14:281-360.*
Rey L, May JC, eds. Freeze Drying/Lyophilization of Pharmaceutical and Biological Products. Informa Healthcare. Drugs and the Pharmaceutical Sciences, vol. 206. 3rd Ed. 2010.*
Pearson FE, McNeilly CL, Crichton ML, Primiero CA, Yukiko SR, Fernando GJ, Chen X, Gilbert SC, Hill AV, Kendall MA. Dry-coated live viral vector vaccines delivered by nanopatch microprojections retain long-term thermostability and induce transgene-specific T cell responses in mice. PLoS One. Jul. 9, 2013;8(7):e67888.*
Croyle MA, Cheng X, Wilson JM. Development of formulations that enhance physical stability of viral vectors for gene therapy. Gene Ther. Sep. 2001;8(17):1281-90.*
Croyle MA, Roessler BJ, Davidson BL, Hilfinger JM, Amidon GL. Factors that influence stability of recombinant adenoviral preparations for human gene therapy. Pharm Dev Technol. Aug. 1998;3(3):373-83.*
Chen S, Guo D, Guo B, Liu J, Shen Y, Xu X, Huang W, Guo S. Investigation on formulation and preparation of adenovirus encoding human endostatin lyophilized powders. Int J Pharm. May 10, 2012;427(2):145-52. Epub Jan. 5, 2012.*
Jha BK, Gupta BP, Maharjan P, Kakshapati S, Munankarmi NN. Effect of Lyophilization on Infectivity and Viral Load of Adenovirus. Nepal J of Biotech. Dec. 2015, vol. 3, No. 1:15-21.*
Malenovská H. The influence of stabilizers and rates of freezing on preserving of structurally different animal viruses during lyophilization and subsequent storage. J Appl Microbiol. Dec. 2014;117(6):1810-9. Epub Nov. 4, 2014.*
Evans RK, Nawrocki DK, Isopi LA, Williams DM, Casimiro DR, Chin S, Chen M, Zhu DM, Shiver JW, Volkin DB. Development of stable liquid formulations for adenovirus-based vaccines. J Pharm Sci. Oct. 2004;93(10):2458-75.*

(Continued)

*Primary Examiner* — Rachel B Gill
(74) *Attorney, Agent, or Firm* — Lisa Matovcik

(57) ABSTRACT

The present invention relates to the formulation of Adenoviral vectors in an aqueous mixture or freeze dried composition in the presence of amorphous sugar and low salt concentration, its formulation as well as a method for obtaining the dried composition.

7 Claims, 9 Drawing Sheets

(56) References Cited

OTHER PUBLICATIONS

P.E. Cruz et al: "Screening of Novel Excipients for Improving the Stability of Retroviral and Adenoviral Vectors", Biotechnology Progress, vol. 22. No. 2, Apr. 7, 2006.
Peruzzi D et al: "A novel Chimpanzee serotype-based adenoviral vector as delivery tool for cancer vaccines", Vaccine. Elsevier Ltd, GB. vol. 27, No. 9, Feb. 25, 2009.
Fred Mathot et al., Development of a Freeze-Dried Ebola-Expressing Adenoviral Vector: Unexpected Findings and Problems Solved, BioProcess international, pp. 26-31, May 2018.
Chatterjee at al., Raffinose crystallization during freeze-drying and its impact on recovery of protein activity, Pharmaceutical Research, Feb. 2005, p. 303-309, vol. 22, No. 2.

\* cited by examiner

PHARMACEUTICAL COMPOSITION COMPRISING AN ADENOVIRAL VECTOR

CROSS-REFERENCE TO RELATED APPLICATIONS

This is the U.S. National Stage application submitted under 35 U.S.C. § 371 for International Application No. PCT/EP2016/067280, filed Jul. 20, 2016, which claims priority to Application No. GB 1513010.7, filed Jul. 23, 2015 all of which are incorporated herein by reference in their entireties.

The present invention relates to the formulation of Adenoviral vectors in an aqueous mixture or freeze dried composition, its formulation as well as a method for obtaining the dried composition.

BACKGROUND

Adenoviral vectors represent a therapeutic protein delivery platform whereby the nucleic acid sequence encoding the therapeutic protein is incorporated into the adenoviral genome, which is brought to expression when the adenoviral particle is administered to the treated subject. It has been a challenge in the art to develop stabilizing formulation for the adenoviral vectors which allow storage at acceptable storage temperatures with a considerable shelf life.

Stabilizing formulations have been reported for Human Adenoviral vectors such as described by R. K Evans et al. ('Development of stable Liquid Formulations for Adenovirus-Based Vaccines' Journal of Pharmaceutical Sciences (2004) Vol. 93, No. 10, 2458-2475). However, there remains a need in the art for formulations preserving the stability of adenoviral vectors.

SUMMARY OF THE INVENTION

The inventors surprisingly found that adenoviral vectors can be particularly sensitive to the presence of salt such as sodium chloride. The invention therefore provides an aqueous mixture and a freeze-dried composition obtained from said aqueous mixture by lyophilization (hereinafter referred to as the "dried composition") having low concentrations of salt, in particular having sodium chloride concentrations at or below 50 mM for formulating the simian adenoviral vectors. The invention also provides a method of using the freeze-dried composition whereby the composition is reconstituted with a low salt aqueous liquid, e.g. water for injection or an aqueous solution of a non-ionic isotonifying agent.

In addition it has been found that including the amorphous sugar trehalose as cryoprotectant has further favourable effects on the stability of the simian adenoviral vector particles. The invention therefore provides the aqueous mixture and dried composition comprising the amorphous sugar trehalose or a combination of trehalose with another amorphous sugar as cryoprotectant.

In a second aspect the present invention provides a method of lyophilisation of adenoviral vector compositions using an annealing step in the freezing phase, thereby substantially increasing the stability of the adenoviral particles during lyophilisation.

DETAILED DESCRIPTION

Figure 1:
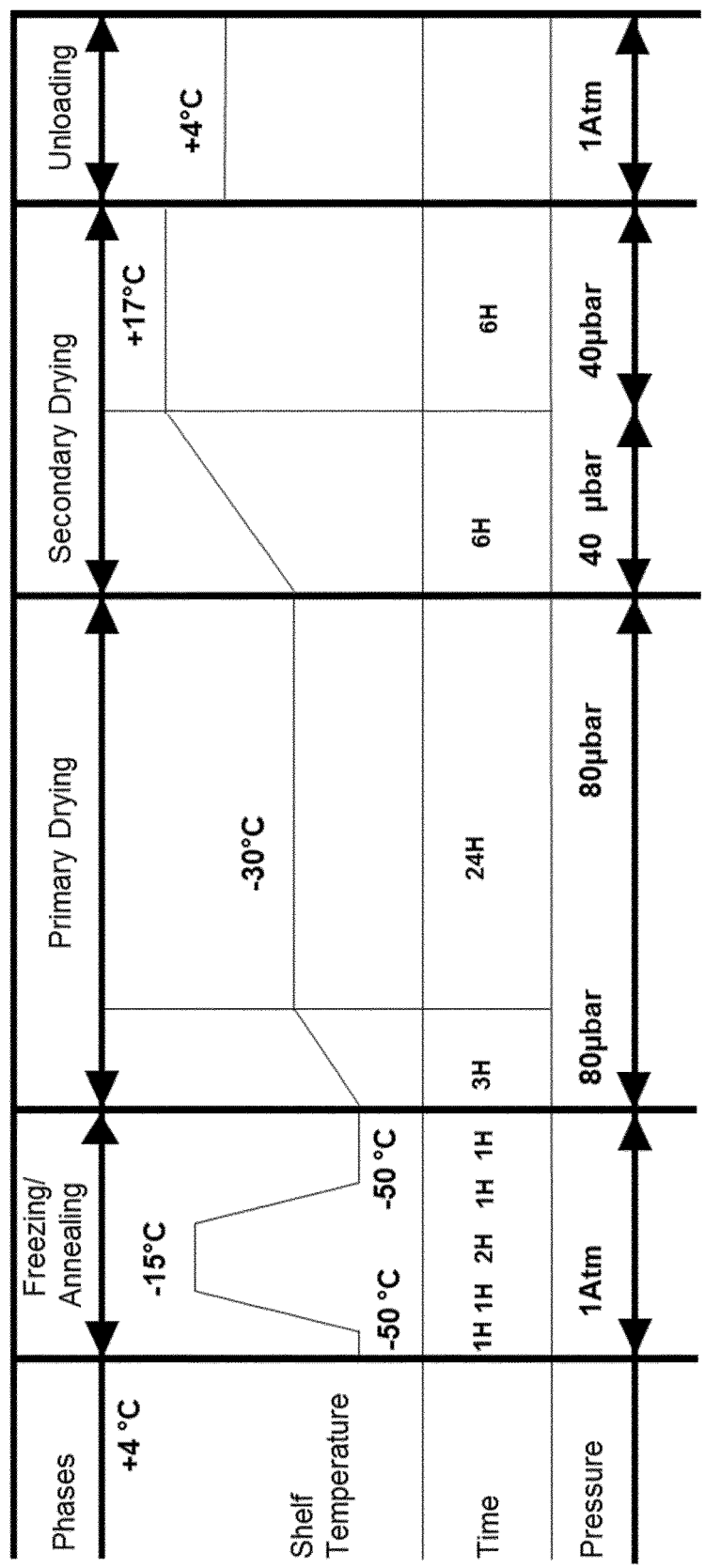
FIG. 1 illustrates the freeze drying cycle used in example 1.

Contrary to reports in the art on the formulation of adenoviral vectors, the inventors found that the stabilizing formulations developed for e.g. Human Adenoviral vectors could not successfully be applied to all adenoviral vectors, e.g. simian adenoviral vectors. The present invention now describes compositions of adenoviral vectors wherein the adenoviral particle's structural integrity and functionality is better protected or maintained.

The novel formulation allows storage of the composition, liquid or dried, at 4° C., 25° C. or 37° C., for up to 1 month, 3 months, 6 months, 1 year, 2 years or 3 years. In one embodiment, the dried composition can be stored at 4° C. for 3 years, at 25° C. for 3 months or at 37° C. for 1 month. It is understood that storage is adequate if at least 50%, at least 60%, at least 70%, at least 80% or at least 90% of the infectivity is retained compared to the infectivity of the starting material.

The mixtures, compositions and methods described herein allow storage of the adenoviral vector for at least 1 month at 37° C., or at least 3 months at 25° C. or at least 3 years at 4° C. whilst retaining at least 50%, at least 60%, at least 70%, at least 80% or at least 90% of the infectivity compared to the infectivity of the starting material.

Stability of the adenoviral vectors can, amongst other methods, be determined by measuring the infectivity of the vector, e.g. retention of infectivity upon manipulation (e.g. freeze drying) or storage of the viral vector. The term "infectivity" refers to the ability of the vector to enter in a susceptible host, i.e. cells, and deliver its genetic material for expression by the host. Infectivity can be expressed as "the 50% cell culture infectious dose" ($CCID_{50}$), which is the amount of adenoviral vector that is required to infect 50% of the cells in a given cell culture. Infectivity can be measured by measuring the proportion of cells wherein an adenoviral transgene is expressed. For example, green fluorescent protein can be used as infectivity marker whereby the number of cells expressing green fluorescent protein after 24 hours of incubation with the vector is determined. Alternatively, infectivity can be measured by determination of the number of cells expressing the adenovirus hexon capsid protein after 24 hours of incubation with the vector.

Adenovirus has been widely used for gene transfer applications due to its ability to achieve highly efficient gene transfer in a variety of target tissues and large transgene capacity. Adenoviral vectors of use in the present invention may be derived from a range of mammalian hosts. Over 100 distinct serotypes of adenovirus have been isolated which infect various mammalian species. These adenoviral serotypes have been categorised into six subgenera (A-F; B is subdivided into B1 and B2) according to sequence homology and on their ability to agglutinate red blood cells (Tatsis and Ertl Molecular Therapy (2004) 10:616-629).

In one embodiment, the adenoviral vector of the present invention is derived from a human adenovirus. Examples of such human-derived adenoviruses are Ad1, Ad2, Ad4, Ad5, Ad6, Ad11, Ad 24, Ad34, Ad35, particularly Ad5, Ad11 and Ad35. Although Ad5-based vectors have been used extensively in a number of gene therapy trials, there may be limitations on the use of Ad5 and other human group C adenoviral vectors due to preexisting immunity in the general population due to natural infection. Ad5 and other human group C members tend to be among the most seroprevalent serotypes. Additionally, immunity to existing vectors may develop as a result of exposure to the vector during treatment. These types of preexisting or developed immunity to seroprevalent vectors may limit the effectiveness of gene therapy or vaccination efforts. Alternative adenovirus serotypes, thus constitute very important targets in the pursuit of gene delivery systems capable of evading the host immune response.

Therefore, in another embodiment, the adenoviral vector of the present invention is derived from a nonhuman simian adenovirus, also referred to simply as a simian adenovirus. Numerous adenoviruses have been isolated from nonhuman simians such as chimpanzees, bonobos, rhesus macaques and gorillas, and vectors derived from these adenoviruses induce strong immune responses to transgenes encoded by these vectors (Colloca et al. (2012) Sci. Transl. Med. 4:1-9; Roy et al. (2004) Virol. 324: 361-372; Roy et al. (2010) J. of Gene Med. 13:17-25). Certain advantages of vectors based on nonhuman simian adenoviruses include the relative lack of cross-neutralising antibodies to these adenoviruses in the target population. For example, cross-reaction of certain chimpanzee adenoviruses with pre-existing neutralizing antibody responses is only present in 2% of the target population compared with 35% in the case of certain candidate human adenovirus vectors.

In specific embodiments, the adenoviral vector is derived from a non-human adenovirus, such as a simian adenovirus and in particular a chimpanzee adenovirus such as ChAd3, ChAd63, ChAd83, ChAd155, Pan 5, Pan 6, Pan 7 (also referred to as C7) or Pan 9. Examples of such strains are described in WO03/000283, WO2010/086189 and GB1510357.5 and are also available from the American Type Culture Collection, 10801 University Boulevard, Manassas, Va. 20110-2209, and other sources. Alternatively, adenoviral vectors may be derived from nonhuman simian adenoviruses isolated from bonobos, such as PanAd1, PanAd2 or PanAd3. Examples of such vectors described herein can be found for example in WO2005/071093 and WO2010/086189. Adenoviral vectors may also be derived from adenoviruses isolated from gorillas as described in WO2013/52799, WO2013/52811 and WO2013/52832.

Adenoviruses have a characteristic morphology with an icosahedral capsid comprising three major proteins, hexon (II), penton base (III) and a knobbed fiber (IV), along with a number of other minor proteins, VI, VIII, IX, IIIa and IVa2. The hexon accounts for the majority of the structural components of the capsid, which consists of 240 trimeric hexon capsomeres and 12 penton bases. The hexon has three conserved double barrels, while the top has three towers, each tower containing a loop from each subunit that forms most of the capsid. The base of hexon is highly conserved between adenoviral serotypes, while the surface loops are variable (Tatsis and Ertl Molecular Therapy (2004) 10:616-629). Penton is another adenoviral capsid protein that forms a pentameric base to which fiber attaches. The trimeric fiber protein protrudes from the penton base at each of the 12 vertices of the capsid and is a knobbed rod-like structure. The primary role of the fiber protein is the tethering of the viral capsid to the cell surface via the interaction of the knob region with a cellular receptor, and variations in the flexible shaft as well as knob regions of fiber are characteristic of the different serotypes (Nicklin et al Molecular Therapy 2005 12:384-393).

Adenoviral vectors may be used to deliver desired RNA or protein sequences, for example heterologous sequences, for in vivo expression. A vector may include any genetic element including naked DNA, a phage, transposon, cosmid, episome, plasmid, or a virus. By "expression cassette" (or "minigene") is meant the combination of a selected heterologous gene (transgene) and the other regulatory elements necessary to drive translation, transcription and/or expression of the gene product in a host cell.

Typically, an adenoviral vector is designed such that the expression cassette is located in a nucleic acid molecule which contains other adenoviral sequences in the region native to a selected adenoviral gene. The expression cassette may be inserted into an existing gene region to disrupt the function of that region, if desired. Alternatively, the expression cassette may be inserted into the site of a partially or fully deleted adenoviral gene. For example, the expression cassette may be located in the site of a mutation, insertion or deletion which renders non-functional at least one gene of a genomic region selected from the group consisting of E1A, E1B, E2A, E2B, E3 and E4. The term "renders non-functional" means that a sufficient amount of the gene region is removed or otherwise disrupted, so that the gene region is no longer capable of producing functional products of gene expression. If desired, the entire gene region may be removed (and suitably replaced with the expression cassette). Suitably, E1 genes of adenovirus are deleted and replaced with an expression cassette consisting of the promoter of choice, cDNA sequence of the gene of interest and a poly A signal, resulting in a replication defective recombinant virus.

In one embodiment, the transgene encoded by the adenoviral vector is a sequence encoding a product which is useful in biology and medicine, such as therapeutic or immunogenic proteins, RNA, enzymes, or catalytic RNAs. Desirable RNA molecules include tRNA, dsRNA, ribosomal RNA, catalytic RNAs, RNA aptamers, and antisense RNAs. One example of a useful RNA sequence is a sequence which extinguishes expression of a targeted nucleic acid sequence in the treated animal.

Thus in one embodiment, the mixture or composition as described herein is for use in prophylactic (thus immunogenic or preventive) or therapeutic treatment of a subject, such as a mammal or human subject, depending on the transgene encoded by the adenoviral vector.

The transgene may encode a polypeptide or protein used for treatment, e.g., of genetic deficiencies, as a cancer therapeutic or vaccine, for induction of an immune response, and/or for prophylactic vaccine purposes. As used herein, induction of an immune response refers to the ability of a protein, also known as an "antigen" or "immunogen", to induce a T cell and/or a humoral immune response to the protein.

Immunogens expressed by the adenoviral vectors formulated as described herein and which are useful to immunize a human or non-human animal against other pathogens include, e.g., bacteria, fungi, parasitic microorganisms or multicellular parasites which infect human and non-human vertebrates, or from a cancer cell or tumor cell. For example, immunogens may be selected from a variety of viral families.

In one embodiment, the immunogen is from a filovirus, for example Ebola (Zaire, Sudan, Reston, Budibugyo and Ivory Coast species) or Marburg. Such antigens may be derived from the viral glycoprotein (transmembrane and/or secreted form) and/or the viral nucleoprotein. Examples of such vectors can be found, inter alia, in WO2011/130627.

In another embodiment, immunogens may be selected from respiratory viruses such as respiratory syncytial virus (RSV) and other paramyxoviruses such as human metapneumovirus, hMPV and parainfluenza viruses (PIV). Suitable antigens of RSV which are useful as immunogens to immunize a human or non-human animal can be selected from: the fusion protein (F), the attachment protein (G), the matrix protein (M2) and the nucleoprotein (N). Such vectors are described in WO2012/089833 and PCT/EP2016/063297. In one embodiment, the ChAd155-RSV construct as disclosed in PCT/EP2016/063297 is considered for the compositions and methods disclosed.

In another embodiment, the immunogen may be from a retrovirus, for example a lentivirus such as the Human Immunodeficiency Virus (HIV). In such an embodiment, immunogens may be derived from HIV-1 or HIV-2 sequences, such as for Gag, Pol, Nef, Env, and others. Such vectors are described, inter alia, in GB1510357.5 and WO2008/107370.

Alternatively or in addition, a transgene sequence may include a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc. These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry.

In addition to the transgene, the expression cassette also may include conventional control elements which are operably linked to the transgene in a manner that permits its transcription, translation and/or expression in a cell transfected with the adenoviral vector. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (poly A) signals including rabbit beta-globin polyA; sequences that stabilize cytoplasmic mRNA; sequences that enhance translation efficiency (e.g., Kozak consensus sequence); sequences that enhance protein stability; and when desired, sequences that enhance secretion of the encoded product. Among other sequences, chimeric introns may be used.

A "promoter" is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A great number of expression control sequences, including promoters which are internal, native, constitutive, inducible and/or tissue-specific, are known in the art and may be utilized.

Adenoviral vectors are generated by the modification of the wild type adenovirus to express heterologous genes (trangenes) and/or delete or inactivate undesirable adenoviral sequences. Adenoviral vectors may also have altered replication competency. For example the vector may be replication defective or have limited replication such that it has a reduced ability to replicate in non-complementing cells, compared to the wild type virus. This may be brought about by mutating the virus e.g. by deleting a gene involved in replication, for example deletion of the E1a, E1b, E3 or E4 gene. Such modifications are known to the skilled person and described in the art, e.g. by Roy et al., Human Gene Therapy 15:519-530, 2004; Colloca et al. (2012) Sci. Transl. Med. 4:1-9; Roy et al. (2004) Virol. 324: 361-372; or WO 03/000283.

These vectors are generated using techniques known to those of skill in the art. Such techniques include conventional cloning techniques of cDNA such as those described in texts, use of overlapping oligonucleotide sequences of the adenovirus genomes, polymerase chain reaction, and any suitable method which provides the desired nucleotide sequence. Particularly suitable methods include standard homologous recombination methods such as those provided in Colloca et al. (2012) Sci. Transl. Med. 4:1-9; Roy et al. (2004) Virol. 324: 361-372; Roy et al. (2010) J. of Gene Med. 13:17-25; and WO2010/085984 or recombineering methods as described in Warming et al. Nuc. Acids Res. (2005) 33:e36.

The adenoviral vectors can be produced on any suitable cell line in which the virus is capable of replication. In particular, complementing cell lines which provide the factors missing from the viral vector that result in its impaired replication characteristics (such as E1) can be used. Without limitation, such a cell line may be HeLa (ATCC Accession No. CCL 2), A549 (ATCC Accession No. CCL 185), HEK 293, KB (CCL 17), Detroit (e.g., Detroit 510, CCL 72) and WI-38 (CCL 75) cells, among others. These cell lines are all available from the American Type Culture Collection, 10801 University Boulevard, Manassas, Va. 20110-2209. Other suitable parent cell lines may be obtained from other sources, such as PER.C6™ cells, as represented by the cells deposited under ECACC no. 96022940 at the European Collection of Animal Cell Cultures (ECACC) at the Centre for Applied Microbiology and Research (CAMR, UK) or Her 96 cells (Crucell).

A particularly suitable complementation cell line is the Procell92 cell line. The Procell 92 cell line is based on HEK 293 cells which express adenoviral E1 genes, transfected with the Tet repressor under control of the human phosphoglycerate kinase-1 (PGK) promoter, and the G418-resistance gene (Vitelli et al. PLOS One (2013) 8(e55435):1-9). Procell92.S is adapted for growth in suspension conditions and is also useful for producing adenoviral vectors expressing toxic proteins (www.Okairos.com/e/inner-s.php?m=00084, last accessed 13 Apr. 2015).

Adenoviral Delivery Methods and Dosage

A mixture or composition as described herein may comprise one or more recombinant vectors capable of inducing an immune response, for example a humoral (e.g., antibody) and/or cell-mediated (e.g., a cytotoxic T cell) response, against a transgene product delivered by the vector following delivery to a mammal, suitably a human. A recombinant adenovirus may comprise (suitably in any of its gene deletions) a gene encoding a desired immunogen and may therefore be used in a vaccine. The recombinant adenoviruses can be used as prophylactic or therapeutic vaccines against any pathogen for which the antigen(s) crucial for induction of an immune response and able to limit the spread of the pathogen has been identified and for which the cDNA is available.

Thus in one embodiment, the mixture and/or composition described herein are for use in immunization of a subject, such as a human subject. The levels of immunity of the selected gene can be monitored to determine the need, if any, for boosters. Following an assessment of antibody titers in the serum, optional booster immunizations may be desired.

Optionally, a mixture or composition of the invention may be formulated to contain other components, including, e.g., adjuvants, stabilizers, pH adjusters, preservatives and the like. Such an adjuvant can be administered with a priming DNA vaccine encoding an antigen to enhance the antigen-specific immune response compared with the immune response generated upon priming with a DNA vaccine encoding the antigen only. Alternatively, such an adjuvant can be administered with a polypeptide antigen which is administered in an administration regimen involving the adenoviral vectors of the invention.

In some embodiments, the mixture or composition as described herein is administered to a subject by intramuscular injection, intravaginal administration, intravenous injection, intraperitoneal injection, subcutaneous injection, epicutaneous administration, intradermal administration, nasal administration or oral administration.

If the therapeutic regimen involves co-administration of one or more adenoviral vectors and/or a further component, these may be coformulated (i.e. in the same mixture or composition) or each formulated in different compositions. When formulated separately, they are favourably administered co-locationally at or near the same site. For example, the components can be administered (e.g. via an administration route selected from intramuscular, transdermal, intradermal, sub-cutaneous) to the same side or extremity ("co-lateral" administration) or to opposite sides or extremities ("contra-lateral" administration).

Dosages of the viral vector will depend primarily on factors such as the condition being treated, the age, weight and health of the patient, and may thus vary among patients. For example, a therapeutically effective adult human or veterinary dosage of the viral vector generally contains $1\times10^5$ to $1\times10^{15}$ viral particles, such as from $1\times10^8$ to $1\times10^{12}$ (e.g., $1\times10^8$, $5\times10^8$, $1\times10^9$, $5\times10^9$, $1\times10^{10}$, $2.5\times10^{10}$, $5\times10^{10}$, $1\times10^{11}$ $5\times10^{11}$, $1\times10^{12}$ particles). Alternatively, a viral vector can be administered at a dose that is typically from $1\times10^5$ to $1\times10^{10}$ plaque forming units (PFU), such as $1\times10^5$ PFU, $5\times10^5$ PFU, $1\times10^6$ PFU, $5\times10^6$ PFU, $1\times10^7$ PFU, $5\times10^7$ PFU, $1\times10^8$ PFU, $5\times10^8$ PFU, $1\times10^9$ PFU, $5\times10^9$ PFU, or $1\times10^{10}$ PFU. Dosages will vary depending upon the size of the animal and the route of administration. For example, a suitable human or veterinary dosage (for about an 80 kg animal) for intramuscular injection is in the range of about $1\times10^9$ to about $5\times10^{12}$ particles per mL, for a single site. Optionally, multiple sites of administration may be used. In another example, a suitable human or veterinary dosage may be in the range of about $1\times10^{11}$ to about $1\times10^{15}$ particles for an oral formulation.

The adenoviral vector can be quantified by Quantitative PCR Analysis (Q-PCR), for example with primers and probe designed on CMV promoter region using as standard curve serial dilution of plasmid DNA containing the vector genome with expression cassette including HCMV promoter. The copy number in the test sample is determined by the parallel line analysis method. Alternative methods for vector particle quantification can be analytical HPLC or spectrophotometric method based on $A_{260}$ nm.

An immunologically effective amount of a nucleic acid may suitably be between 1 ng and 100 mg. For example, a suitable amount can be from 1 µg to 100 mg. An appropriate amount of the particular nucleic acid (e.g., vector) can readily be determined by those of skill in the art. Exemplary effective amounts of a nucleic acid component can be between 1 ng and 100 µg, such as between 1 ng and 1 µg (e.g., 100 ng-1 µg), or between 1 µg and 100 µg, such as 10 ng, 50 ng, 100 ng, 150 ng, 200 ng, 250 ng, 500 ng, 750 ng, or 1 µg. Effective amounts of a nucleic acid can also include from 1 µg to 500 µg, such as between 1 µg and 200 µg, such as between 10 and 100 µg, for example 1 µg, 2 g, 5 µg, 10 µg, 20 µg, 50 µg, 75 µg, 100 µg, 150 µg, or 200 µg. Alternatively, an exemplary effective amount of a nucleic acid can be between 100 µg and 1 mg, such as from 100 µg to 500 µg, for example, 100 µg, 150 µg, 200 µg, 250 µg, 300 µg, 400 µg, 500 µg, 600 µg, 700 µg, 800 µg, 900 µg or 1 mg.

Generally a human dose will be contained in a volume of between 0.5 ml and 2 ml. Thus the mixture and/or composition described herein can be formulated such that a volume of, for example 0.5, 1.0, 1.5 or 2.0 ml human dose per individual or combined immunogenic components is administered.

One of skill in the art may adjust these doses, depending on the route of administration and the therapeutic or vaccine application for which the recombinant vector is employed. The levels of expression of the transgene, or for an adjuvant, the level of circulating antibody, can be monitored to determine the frequency of dosage administration.

If one or more priming and/or boosting steps are used, this step may include a single dose that is administered hourly, daily, weekly or monthly, or yearly. As an example, mammals may receive one or two doses containing between about 10 μg to about 50 μg of plasmid in carrier. The amount or site of delivery is desirably selected based upon the identity and condition of the mammal.

The therapeutic levels of, or level of immune response against, the protein encoded by the selected transgene can be monitored to determine the need, if any, for boosters. Following an assessment of CD8+ T cell response, or optionally, antibody titers, in the serum, optional booster immunizations may be desired. Optionally, the adenoviral vector may be delivered in a single administration or in various combination regimens, e.g., in combination with a regimen or course of treatment involving other active ingredients or in a prime-boost regimen.

The inventors found that adenoviral vectors can be substantially impacted by the presence of salt, such as sodium chloride, either when in dry or when in liquid form. The invention thus relates to formulations, i.e. liquid mixtures and dried compositions, taken into account the sensitivity of adenoviral vectors to salt, such as sodium chloride. In one embodiment, simian adenoviral vectors are formulated using the liquid mixtures and compositions described herein.

The term "salt" as used herein refers to ionic compounds that result from the neutralization reaction of an acid and a base, composed of a related number of cations and anions such that the product is without net charge, for example sodium chloride. The component ions can either be inorganic or organic, and, can be monoatomic or polyatomic.

Therefore according to one embodiment, the amount of salt, in particular the amount of NaCl, present in the aqueous mixture is defined to be less than 50 mM, less than 40 mM, less than 30 mM, less than 20 mM, less than 15 mM, less than 10 mM, or, less than 7.5 mM. Preferably the composition is not completely devoid of salt or not completely devoid of sodium chloride. Therefore according to an embodiment of the invention, salt, in particular sodium chloride, is present in an amount of at least 0.5 mM, at least 1 mM, at least 2 mM, at least 3 mM, or, at least 4 mM. Alternatively, sodium chloride is present in an amount between 1 and 50 mM, between 2.5 and 25 mM, between 2.5 and 15 mM, between 2.5 and 10 mM or between 2.5 and 7.5 mM. According to a particular embodiment, sodium chloride is present in an amount of about 5 mM.

For the purpose of defining ranges, the term "between" as used herein is considered to include the end points of the range. For example, when sodium chloride is said to be present in an amount between 2.5 and 10 mM, those formulations wherein NaCl is present at a concentration of 2.5 mM or 10 mM are included.

According to further embodiments, also the salt, such as sodium chloride, content of the aqueous liquid for reconstituting the dried composition is defined. According to one embodiment the amount of salt, e.g. sodium chloride, present in the aqueous liquid for reconstituting is less than 50 mM, less than 40 mM, less than 30 mM, less than 20 mM, less than 15 mM, less than 10 mM, or, less than 7.5 mM.

The aqueous liquid for reconstituting the lyophilized composition may be essentially free of salt such as essentially free of sodium chloride. By essentially free is meant that the concentration of salt or sodium chloride is at or very near to zero mM.

In a further embodiment, the aqueous liquid for reconstituting the composition is not completely devoid of salt or sodium chloride. Accordingly, salt, such as sodium chloride, can be present in the aqueous liquid used for reconstituting the dried composition in an amount of at least 0.5 mM, at least 1 mM, at least 2 mM, at least 3 mM, or, at least 4 mM. Alternatively, salt, such as sodium chloride, is present in the aqueous liquid used for reconstituting the composition in an amount between 1 and 50 mM, between 2.5 and 25 mM, between 2.5 and 15 mM, between 2.5 and 10 mM or between 2.5 and 7.5 mM. According to a particular embodiment, salt, such as sodium chloride, is present in the aqueous liquid used for reconstituting the composition in an amount of 5 mM.

The invention thus also provides a method of using the dried composition as described herein, wherein the dried composition is reconstituted with an aqueous liquid for reconstituting the composition as defined herein.

The term "cryoprotectant" refers to a class of excipients which prevents freeze damage of what is being frozen, in casu, the adenoviral vector.

A cryoprotectant suitable for use in the present invention is an amorphous sugar such as one selected from sucrose, trehalose, mannose, mannitol, raffinose, lactitol, sorbitol and lactobionic acid, glucose, maltulose, iso-maltulose, lactulose, maltose, lactose, isomaltose, maltitol, palatinit, stachyose, melezitose, dextran, or, a combination thereof. In one embodiment, the cryoprotectant is an amorphous sugar selected from sucrose, trehalose, lactose, raffinose, dextran, mannitol and combinations thereof.

In a specific embodiment, the cryoprotectant or amorphous sugar is trehalose, sucrose or trehalose in combination with a second amorphous sugar such as selected from sucrose, lactose, raffinose, dextran and mannitol. Alternatively, the cryoprotectant is trehalose, sucrose or combination of sucrose and trehalose. In another embodiment, the cryoprotectant is trehalose or trehalose in combination with sucrose. In yet another embodiment, the cryoprotectant is trehalose.

The cryoprotectant as selected according to the embodiments herein may be present in defined amounts. In an embodiment, the aqueous mixture contains at least 2.5% (w/v), at least 3% (w/v), at least 3.5% (w/v), at least 4% (w/v), at least 4.5% (w/v), at least 5% (w/v), or at least 6% (w/v) of the cryoprotectant as selected herein above. In another embodiment the cryoprotectant is present in the aqueous mixture in a total amount of less than 17.5% (w/v), such as less than 15% (w/v), less than 12.5% (w/v), less than 11% (w/v), less than 10% (w/v), or less than 9.5% (w/v). Alternatively stated, the cryoprotectant is present in the aqueous mixture in a total amount of at least 4%, at least 4.5% or at least 5% (w/v %), but less than 15%, less than 12.5%, less than 11% or less than 10% (w/v %).

The total concentration of cryoprotectant in the aqueous mixture suitably ranges from 5 to 10% (w/v). In one embodiment, at least 5%, between 5 and 15% or between 5 and 10% (w/v %) trehalose is used. In one embodiment, 8%, 8.5%, 9% or 9.25% trehalose is used. In specific embodiments, the aqueous mixture comprises at least 5% (w/v %) or between 5 and 10% (w/v %) of sucrose, trehalose or a combination thereof. In another specific embodiment, the aqueous mixture comprises at least 5% (w/V) trehalose, optionally further comprising sucrose, lactose, raffinose, dextran and mannitol.

The aqueous mixture or dried composition may further include a surfactant selected from poloxamer surfactants (e.g. poloxamer 188), polysorbate surfactants (e.g. polysorbate 80 and/or polysorbate 20), octoxinal surfactants, polidocanol surfactants, polyoxyl stearate surfactants, polyoxyl castor oil surfactants, N-octyl-glucoside surfactants, macrogol 15 hydroxy stearate, and combinations thereof. In an embodiment, the surfactant is selected from poloxamer surfactants (e.g. poloxamer 188), polysorbate surfactants (e.g. polysorbate 80 and/or polysorbate 20), in particular polysorbate surfactants such as polysorbate 80.

In one embodiment, the surfactant is present in an amount of at least 0.001%, at least 0.005%, at least 0.01% (w/v), and/or up to 0.5% (w/v) as calculated with respect to the aqueous mixture. The surfactant can be present in an amount less than 0.25% or less than 0.1% (w/v). In another embodiment, the surfactant is present in an amount of 0.02% (w/v).

According to specific embodiments, the surfactant is polysorbate 80 or poloxamer 188 present in the aqueous mixture in an amount between 0.005% and 0.5% (w/v), such as about 0.02% (w/v).

In a further embodiment, a buffer is added to the aqueous mixture or dried composition. The pH is typically adjusted in view of the therapeutic components of the composition. Suitably, the pH of the aqueous mixture is at least 6, at least 6.5, at least 7 or at least 7.5. Alternatively stated, the pH of the aqueous mixture may be less than 10, less than 9.5, less than 9 or less than 8.5. In other embodiments, pH of the aqueous mixture is between 6 and 10, between 7 and 9.5, between 7.5 and 9.5, or, about 7.5, for example 7.5+/−0.5, or, 8.5+/−0.5. The optimal pH is in part also determined by the specific adenoviral vector formulated and/or the transgene incorporated therein.

An appropriate buffer may be selected from Tris, succinate, borate, Tris-maleate, lysine, histidine, glycine, glycylglycine, citrate, carbonate or combinations thereof. In one embodiment, the buffer is Tris, succinate or borate. In a further embodiment, the buffer is Tris.

The buffer can be present in the aqueous mixture in an amount of at least 0.5 mM, at least 1 mM, at least 2 mM or at least 5 mM. Or, the buffer can be present in the aqueous mixture in an amount of less than 50 mM, less than 40 mM, less than 30 mM or less than 20 mM. For example, the buffer may be present in an amount of 0.5 mM to 50 mM, 1 mM to 50 mM or 2 mM to 20 mM. In one embodiment, the buffer is present in an amount of about 10 mM.

According to specific embodiments, the buffer is Tris, present in the aqueous mixture in an amount between 2 and 20 mM, such as at about 10 mM.

In an embodiment, the composition also comprises histidine in an amount of up to or about 20 mM, such as at a concentration of about 10 mM.

According to further embodiments, the composition also comprises bivalent metal ions, such as $Mg^{2+}$, $Ca^{2+}$ or $Mg^{2+}$ in the form of a salt, such as $MgCl_2$, $CaCl_2$ or $MgSO_4$. In one embodiment the bivalent metal ion is $Mg^{2+}$. Typical amounts wherein the bivalent metal ions are present in the aqueous mixture are between 0.5 and 10 mM, such as 1 or 2 mM, or 1 mM in particular.

For the purpose of describing embodiments of the invention, the specified amounts of excipients considered for inclusion in the composition (i.e. salt, sodium chloride, cryoprotectant, buffer, surfactant and others described herein) are typically (and unless otherwise indicated) expressed as w/v % calculated with respect to the volume of the aqueous mixture. Alternatively, in case the aqueous mixture is freeze-dried and reconstituted, the amount of excipients may be expressed as w/v % calculated relative to the volume of the reconstituted composition.

In one embodiment, the aqueous mixture and/or (freeze-dried) compositions described herein may be administered to a mammal, e.g. to a human subject. In particular, those mixtures or compositions comprising adenoviral vector encoding a transgene (i.e. a recombinant adenoviral vector) that is a therapeutic or immunogenic protein are considered for formulation in the aqueous mixture or freeze-dried compositions described herein.

The aqueous mixture or dried composition may be contained in a glass vial, either siliconised or non-siliconised. In one embodiment, the aqueous mixture or dried composition are provided in a non-siliconised vial. Suitable, the aqueous mixture can be contained in a non-siliconised vial and freeze-dried when contained in that vial.

The invention also provides a method for lyophilising a liquid containing an adenoviral vector, such as the aqueous mixture as defined herein, to obtain a dry composition, comprising an annealing step. Lyophilisation or freeze-drying cycle usually consists of three process phases. In the first phase of the process, a mostly aqueous solution or mixture is frozen. Subsequently, water is removed first by sublimation during primary drying. In the third phase, non-frozen water is removed by diffusion and desorption during secondary drying. The inventors now found that the introduction of an annealing step during the freezing phase of the lyophilisation cycle, has an unexpected positive impact on the stability of the adenoviral vector.

Accordingly, the invention also provides a method for freeze-drying a liquid containing an adenoviral vector, such as the aqueous mixture as described herein, whereby the freezing step of the freeze-drying cycle comprises an annealing step.

For the purpose of defining the method described the following terms are used as they are known in the art. The term "glass transition temperature" or "Tg" is the temperature at which an amorphous solid becomes soft upon heating or brittle upon cooling. The term "Tg'" refers to the glass transition temperature in the frozen state. The term "collapse temperature" or "Tc" refers to the temperature at which an amorphous material softens to the extent that it can no longer support its own structure. The terms "freeze-drying" and "lyophilising", and, "freeze-dried" and "lyophilised" are used interchangeably and refer to the same process of rapidly freezing a wet substance, followed by dehydration under reduced pressure.

The term "annealing step" as used herein, refers to a method step in freeze-drying cycles of a composition, wherein during the freezing phase the product is maintained at a specified subfreezing temperature for a predetermined period of time. As is known to the skilled person, annealing will lead to Oswald ripening of the ice crystals and cryo-concentration of the amorphous matrix. Typically, the annealing temperature is (slightly) above Tg'. In one embodiment, annealing is executed at a temperature between (Tg'+0.5° C.) and (Tg'+20° C.), e.g. at temperature of −15° C.+/−9° C. or −15° C.+/−6° C., or between (Tg'+0.5° C.) and (Tg'+10° C.). In any case, the annealing temperature should be between Tg' and the melting temperature (Tm) during annealing. In specific embodiments, annealing is done at a temperature between −4° C. and −24° C., alternatively between −4° C. and −20° C., alternatively between −4° C. and −15° C., or alternatively between −8° C. and −15° C. Annealing can be done during the freezing of the product, i.e. whilst the frozen sample is being formed, provided the product is frozen (solid state) and in a glassy state (below Tg'). Alternatively, annealing is done post freezing of the product.

In a specific embodiment, the annealing temperature is about −10° C. (e.g. −10° C.+/−1° C.), more in particular where the aqueous mixture comprises about or at least 9% (w/v) trehalose.

In an embodiment, the product is frozen (i.e. product temperature below Tg') prior to the annealing step. In an embodiment, freezing is achieved by exposing the sample or aqueous mixture to a constant shelf temperature at a freezing temperature which is below Tg'. In an alternative embodiment, the product may be frozen by applying shelf-ramp freezing, i.e. gradually reducing the shelf temperature to a freezing temperature below Tg'. According to embodiments, the freezing temperature is a temperature below Tg' minus 5° C., below Tg' minus 7.5° C., or below Tg' minus 10° C., such as at or below −50° C. According to an embodiment, the product temperature (i.e. the temperature of the sample in the freeze-drier) at the time the freeze-drying cycle is started is between +2° C. and +8° C.

When applying shelf-ramp freezing, the temperature is reduced at a rate of at least 0.1° C./min, at least 0.2° C./min, at least 0.3° C./min or at least 0.5° C./min, and/or a rate of less than 10° C./min, 7.5° C./min, 5° C./min or less than 3° C./min. Alternatively, the temperature is reduced at a rate of 0.1 to 10° C./min, 0.1 to 5° C./min, 0.2 to 3° C./min, or 0.3 to 1° C./min. According to further embodiments, the shelf temperature reached is maintained for about or at least 1 hour (or 60 minutes).

In a further embodiment to the situation where the product is frozen before applying the annealing step, following the initial freezing of the sample or product, the shelf temperature is increased to a temperature above Tg' to initiate the annealing step, such as to a temperature above Tg' plus 0.5° C., above Tg' plus 1° C., above Tg' plus 3° C., above Tg' plus 5° C., above Tg' plus 10° C. or above Tg' plus 20° C. In any case, the temperature is kept below Tm during annealing. In an embodiment, the temperature is raised at a rate of at least 0.1° C./min, at least 0.2° C./min, at least 0.3° C./min or at least 0.5° C./min, and/or a rate of less than 10° C./min, 7.5° C./min, 5° C./min or less than 3° C./min. Alternatively, the temperature is raised at a rate of 0.1 to 10° C./min, 0.1 to 5° C./min, 0.2 to 3° C./min, or 0.3 to 1° C./min. According to further embodiments, the annealing temperature is maintained for at least 2 and/or up to 4 hours.

In a further embodiment, following the annealing step, the shelf temperature is reduced to a temperature below Tg' prior to initiating the drying under reduced pressure, such as to a temperature below Tg' minus 5° C., below Tg' minus 7.5° C., or below Tg' minus 10° C., such as at or below −50° C. In an embodiment, to reach this, the temperature is reduced at a rate of at least 0.1° C./min, at least 0.2° C./min, at least 0.3° C./min or at least 0.5° C./min, and/or a rate of less than 10° C./min, less than 7.5° C./min, less than 5° C./min or less than 3° C./min. Alternatively, the temperature is reduced at a rate of 0.1 to 10° C./min, 0.1 to 5° C./min, 0.2 to 3° C./min, or 0.3 to 1° C./min. According to further embodiments, the shelf temperature reached is maintained for about or at least 1 hour (or 60 minutes).

Drying under reduced pressure as contemplated in step b.ii. of the lyophilisation method described herein will typically be done in two phases, i.e. primary drying and secondary drying. In an embodiment, step b.ii. of the method will include:
   Step b.ii.1. for primary drying at a temperature below Tc of the product, and,
   Step b.ii.2. for secondary drying at a temperature above Tc of the product and below the Tg of the product.

In a further embodiment, primary drying is done at a pressure lower than 90 µbar and/or above 40 µbar. Primary drying conditions may be applied for up to 24 hours or longer.

Another embodiment relates to the secondary drying temperature being achieved by raising the shelf temperature at a rate of 0.1° C./min, at least 0.2° C./min, at least 0.3° C./min or at least 0.5° C./min, and/or a rate of less than 3° C./min, less than 2° C./min, or less than 1° C./min. Alternatively, secondary drying temperature is achieved by raising the shelf temperature at a rate of 0.1 to 3° C./min, 0.2 to 2° C./min, or 0.3 to 1° C./min. According to yet another embodiment the secondary drying temperature is at least −10° C. and/or below 25° C. Secondary drying conditions may be applied for at least or for about 3 hours, at least 4 hours, at least 5 hours, or, at least or for about 6 hours.

The present invention will now be further described by means of the following non-limiting examples.

EXAMPLES

Example 1

Figure 2:
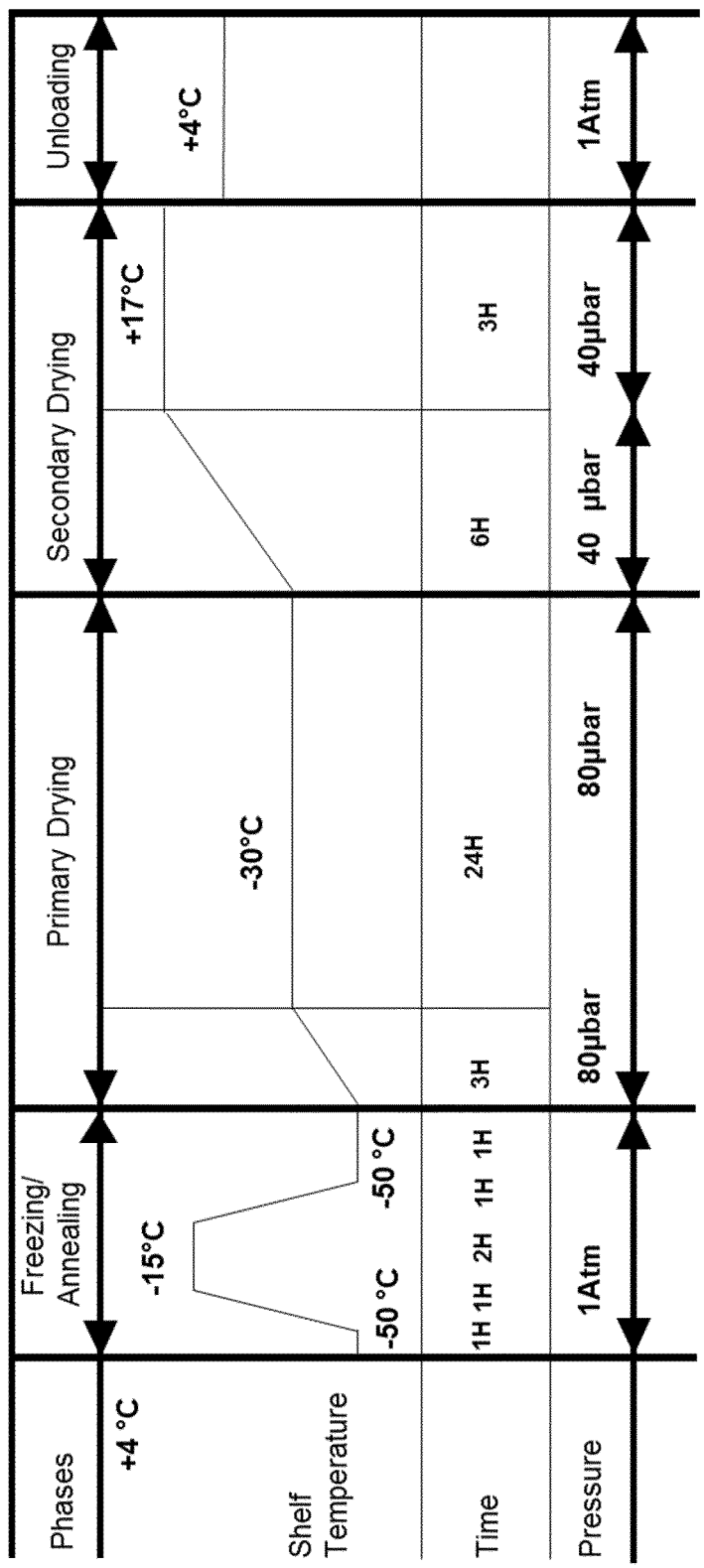
FIG. 2 illustrates the freeze drying cycle used in example 2.

The goal of the experiment was to evaluate the impact of an annealing step in the freeze drying cycle on the titer of ChAd3 expressing green fluorescent protein (GFP). The ChAd3 particles were formulated in an aqueous mixture further comprising the excipients Tris 10 mM (pH 7.4)—histidine 10 mM—MgCl2.6H2O 1 mM—Tween 80 0.02% (m/V)—25 mM NaCl—8% Sucrose (m/V). The concentration of the viral particles was $2.5 \cdot 10^{10}$ vp/ml. After the formulation step, 3 ml non-siliconized type 1 glass vials were filled using 0.5 ml±0.05 of the aqueous mixture. Then the vials were partially sealed with a Helvoet FM460 bromobutyl stopper inserted in freeze drying position (partially inserted to allow water vapour to escape during the freeze drying cycle). Half of the samples were transferred into the freeze dryer chamber and subjected to the freeze drying cycle comprising an annealing step (as shown in FIG. 2) and which is composed of the following steps:
   1. Freezing:
   The shelf temperature was set at −52° C. The filled vials were loaded into the freeze dryer when the shelf temperature was at or lower than −45° C. The samples were then cooled at −52° C. for a minimum of 1 hour.
   2. Annealing step:
   (1) The shelf temperature was raised to reach the target annealing temperature (−15° C.) in one hour
   (2) The annealing temperature was maintained for 2 hours
   (3) The shelf temperature was reduced again from −15° C. to −50° C. in the course of one hour.
   (4) the product was maintained at −50° C. for at least 1 hour
   3. Primary drying:
   The chamber pressure was set at 80 µbar and the shelf temperature was raised from −52° C. to −30° C. over 3 hours. Shelf temperature and chamber pressure were maintained for 24 hours.
   4. Secondary drying:
   The shelf temperature was raised from −30° C. to 17° C. over 6 hours, whilst the chamber pressure was reduced at 40 µbar. When the shelf temperature reached 17° C., these conditions were maintained for 6 hours.

At the end of the freeze drying cycle, the chamber was filled with dry nitrogen until a chamber pressure of 825 mbar was reached, then the stoppers were fully inserted into the vials (stoppering). Once stoppering was completed, the chamber pressure was equilibrated to atmospheric pressure for unloading. The chamber temperature was maintained at +2 to +8° C. until the vials were unloaded. The vials were then unloaded and oversealed with aluminium flip off caps.

In order to assess the impact of the annealing step, the second half of the filled vials was loaded into the freeze dryer chamber between step 2.(3) and step 2.(4) of the freeze drying cycle.

The results of this experiment are presented in the table below:

| sample type | PicoGreen® - free DNA (%) | qPCR -Dnase- (VP/ml) | Infectivity (% GFP) | qPCR/ infectivity | Infectivity preserved (%) |
|---|---|---|---|---|---|
| Without annealing | 57.7 | 1.83E+10 | 5.265 | 3.47E+09 | 93.6 |
| With annealing | 53.4 | 1.96E+10 | 34.71 | 5.66E+08 | 99.5 |
| Control fresh purified bulk | 0 | 2.38E+10 | 72.09 | 3.30E+08 | 100 |
| Control damaged purified bulk | 100 | 1.19E+10 | 0.24 | 4.96E+10 | 0 |

Quantitative PCR (qPCR) as reported herein allows to determine the virus content. The test targets the hCMV promoter present in the adenovirus. The DNA sample was extracted with Quiagen QIAmp 96 DNA Blood.

The PicoGreen® assay measures degradation of the viral particles. Quant-iT™ PicoGreen®® dsDNA reagent is an ultra sensitive fluorescent nucleic acid stain for quantifying double stranded DNA in solution.

The infectivity is determined on the basis of the amount of transgene expressed, which for the present example is GFP. The assay will measure cells expressing GFP after 24 h of infection using flow cytometric detection.

Example 2

The goal of this experiment was to evaluate the impact of an annealing step in the freeze drying cycle on the titer of ChAd3 expressing eGFP. The ChAd3 particles were formulated in an aqueous mixture further comprising the excipients Tris 10 mM (pH 7.4)—histidine 10 mM—$MgCl_2.6H_2O$ 1 mM-Tween 80 0.02% (w/V)—25 mM NaCl—8% Sucrose (w/V). The concentration of the viral particles was $2.5 \cdot 10^{10}$ vp/ml. After the formulation step, 3 ml non-siliconized type 1 glass vials were filled using 0.5 ml±0.05 of the aqueous mixture. Then the vials were partially sealed with a Helvoet FM460 bromobutyl stopper inserted in freeze drying position (partially inserted to allow water vapour to escape during the freeze drying cycle). Half of the samples were transferred into the freeze dryer chamber and subjected to the freeze drying cycle comprising an annealing step (as shown in FIG. 2) and which is composed of the following steps:

1. Freezing:
The shelf temperature was set at −52° C. The filled vials were loaded into the freeze dryer when the shelf temperature was at or lower than −45° C. The samples were then cooled at −52° C. for a minimum of 1 hour.

2. Annealing step:
(1) The shelf temperature was raised to reach the target annealing temperature (−15° C.) in one hour
(2) The annealing temperature was maintained for 2 hours
(3) The shelf temperature was reduced again from −15° C. to −50° C. in the course of one hour.
(4) the product was maintained at −50° C. for at least 1 hour 3. Primary drying:
The chamber pressure was set at 80 μbar and the shelf temperature was raised from −52° C. to −30° C. over 3 hours. Shelf temperature and chamber pressure were maintained for 24 hours.

4. Secondary drying:
The shelf temperature was raised from −30° C. to 17° C. over 6 hours, whilst the chamber pressure was reduced to 40 μbar. When the shelf temperature reached 17° C., these conditions were maintained for 3 hours.

At the end of the freeze drying cycle, the chamber was filled with dry nitrogen until a chamber pressure of 825 mbar was reached. The vials were stoppered once stoppering was completed, the chamber pressure was equilibrated to atmospheric pressure for unloading. The chamber temperature was maintained at +2 to +8° C. until the vials were unloaded. The vials were then unloaded and oversealed with aluminium flip off caps.

In order to compare annealed samples to non-annealed ones, with the same freeze drying cycle, the second half of the filled vials was loaded inside the freeze dryer chamber between step 2.(3) and step 2.(4) of the freeze drying cycle.

The results of this experiment are presented in the table under below:

| Sample type | Concentration formulation (VP/ml) after reconstitution | PicoGreen® - free DNA (%) | qPCR - Dnase- (VP/ml) | Infectivity (% GFP) | qPCR/ infectivity | Infectivity preserved (%) |
|---|---|---|---|---|---|---|
| Without annealing | 2.00E+10 | 61.6 | 1.95E+10 | 2.245 | 8.66E+09 | 83.1 |
| With annealing | 2.00E+10 | 51.2 | 1.90E+10 | 33.14 | 5.73E+08 | 99.5 |
| Ctrl adenoviral stock | 2.00E+10 | 0 | 2.38E+10 | 72.09 | 3.30E+08 | 100 |
| Ctrl adenooviral stock degraded 30' at 60° C. | 2.00E+10 | 100 | 1.19E+10 | 0.24 | 4.96E+10 | 0 | qPCR, Infectivity and PicoGreen® measurements were as described for example 1.

Example 3

The goal of the experiment was to evaluate the stability of an adenoviral vector when formulated in the presence of different amounts of NaCl, ranging from 0 to 50 mM. Isotonicity was maintained by the complementary addition of sucrose. In the ChAd3Eboz construct, the adenoviral vector used in the present experiment, Chimpanzee Adenovirus 3 is used as the vector encoding a Zaire strain Ebola glycoprotein (as described in WO2011/130627). Thus, the conditions listed in Table 1 were tested using a dose of ChAd3Eboz of $5.0 \cdot 10^9$ vp/ml.

Samples were maintained at 30° C. for 3 days after which the impact on the stability of the adenoviral particles was evaluated using qPCR (measuring the viral content by targeting the promoter sequence) and Infectivity (measuring the infectivity of the adenoviral particles by flow cytometric detection of cells stained for adenovirus hexon capsid protein after 24 hours of infection). Results of the test are listed in Table 1.

After storage of the dried composition for 2 month at 4° C. (T2m4): NaCl 150 mM, sucrose 9.25%, trehalose 9.25% and water for injection.

Two samples of bulk ChAd3Eboz, both before and after treatment for 30 mins at 60° C., were used as positive and negative control respectively.

Capsid disruption upon reconstitution of the dried composition was assessed using the PicoGreen® assay. Quant-iT™ PicoGreen® is an ultra-sensitive fluorescent nucleic acid for quantifying double stranded DNA in solution.

Figure 4:
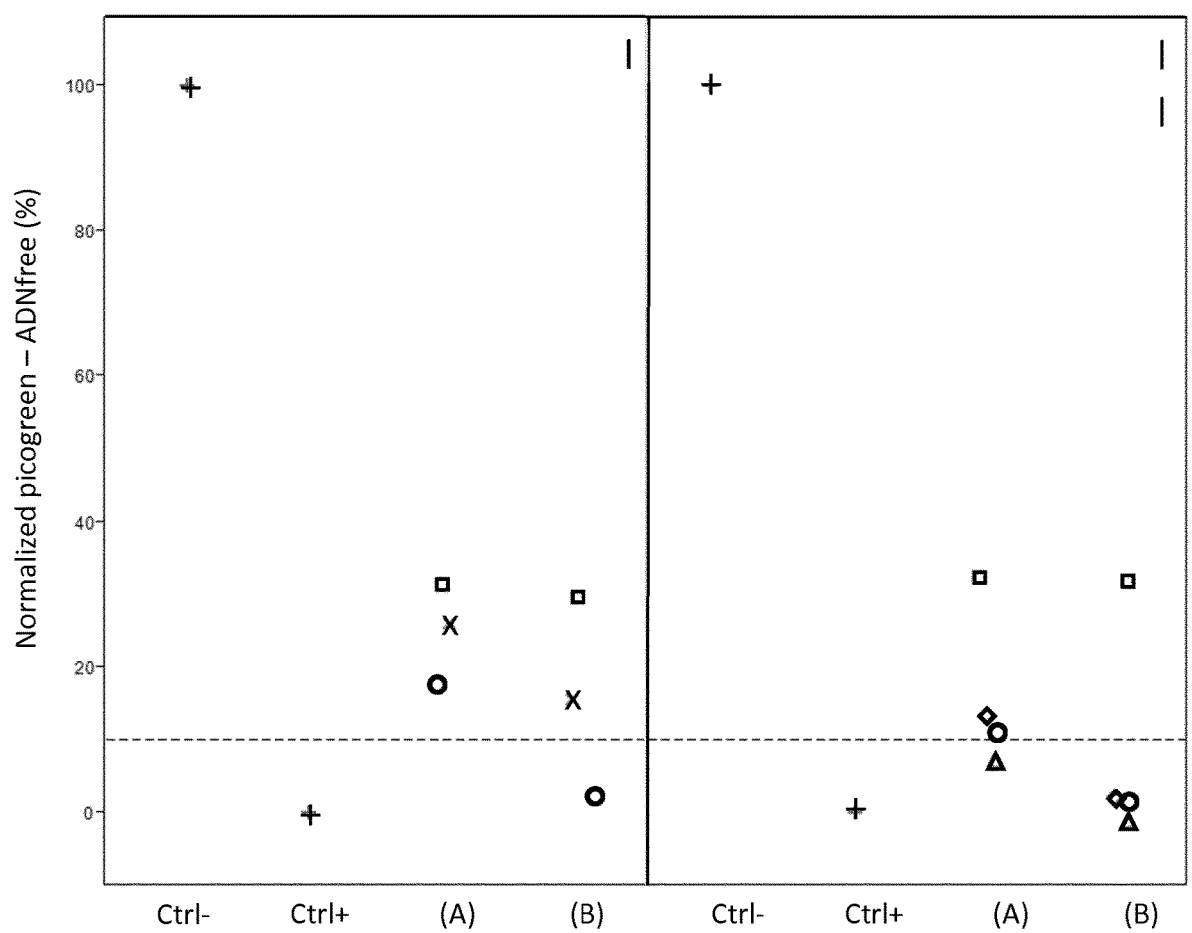
FIG. 4 illustrates the PicoGreen®® data as obtained in experiment 5: ○—water for injection (WFI), x—NaCl 30 mM, □—NaCl 150 mM, ◊—sucrose 9.25%, Δ—trehalose 9.25%; Panel I—at T1m4; Panel II—at T2m4.

As shown in the graph of FIG. 4.I (timepoint T1m4° C.), free DNA in the external phase was directly proportional to the NaCl concentration of the rehydration medium

TABLE 1

|  | qPCR (vp/ml) | qPCR normalized (%) | Infectivity (vp/ml) | Infectivity normalized (%) | qPCR/ infectivity EBOZ |
|---|---|---|---|---|---|
| NaCl 0 mM/sucrose 9.25% | 2.69E+09 | −48.8358 | 15848932 | 631.1253 | 169.4402 |
| NaCl 5 mM/sucrose 9.00% | 3.29E+09 | 726.3484 | 1.26E+08 | 5013.426 | 26.10772 |
| NaCl 10 mM/sucrose 8.70% | 2.73E+09 | 4.700141 | 1584893 | 63.08406 | 1720.605 |
| NaCl 15 mM/sucrose 8.43% | 1.9E+09 | −1057.23 | 3162278 | 125.9007 | 601.85 |
| NaCl 20 mM/sucrose 8.14% | 1.73E+09 | −1278.7 | 1000000 | 39.79168 | 1731.424 |
| NaCl 25 mM/sucrose 7.88% | 2.71E+09 | −22.3824 | 1258925 | 50.10294 | 2149.425 |
| NaCl 50 mM/sucrose 6.50% | 1.32E+09 | −1808.77 | 630957.3 | 25.09518 | 2092.434 |
| Ctrl adenoviral stock | 2.8E+09 | 100 | 2511886 | 100 | 1115.058 |
| Ctrl adenooviral stock degraded 30' at 60° C. | 2.72E+09 | 0 | 794.3282 | 1.88E−15 | 3428467 | qPCR, Infectivity and PicoGreen® measurements were as described for example 1.

Example 4

In the present example, three compositions (composition (a), (b) and (c)) were evaluated by Dynamic Light Scattering (DLS), each following three different storage conditions of the freeze-dried product. The storage conditions tested were 1 month at 4° C. (T1m4), 1 week at 25° C. (T1w25) and 3 days at 37° C. (T3d37). The freeze-drying cycle applied is the same as for example 1 (FIG. 1).
Composition (a): ChAd3Eboz $1 \cdot 10^{11}$ vp/ml, Tris 10 mM pH 7.5, histidine 10 mM, NaCl 25 mM, sucrose 8%, MgCl$_2$ 1 mM, polysorbate 80 0.02%
Composition (b): ChAd3Eboz $1 \cdot 10^{11}$ vp/ml, Tris 10 mM pH 7.5, histidine 10 mM, NaCl 6 mM (residual), trehalose 7%, sucrose 2% (residual), MgCl$_2$ 1 mM, polysorbate 80 0.02%
Composition (c): ChAd3Eboz $1 \cdot 10^{11}$ vp/ml, Tris 10 mM pH 7.5, histidine 10 mM, NaCl 6 mM (residual), trehalose 7%, sucrose 2% (residual), MgCl$_2$ 1 mM, poloxamer 188 0.15%

Two samples of ChAd3Eboz starting material, before and after treatment for 30 minutes at 60° C., were used as positive and negative control respectively.

Figure 3:
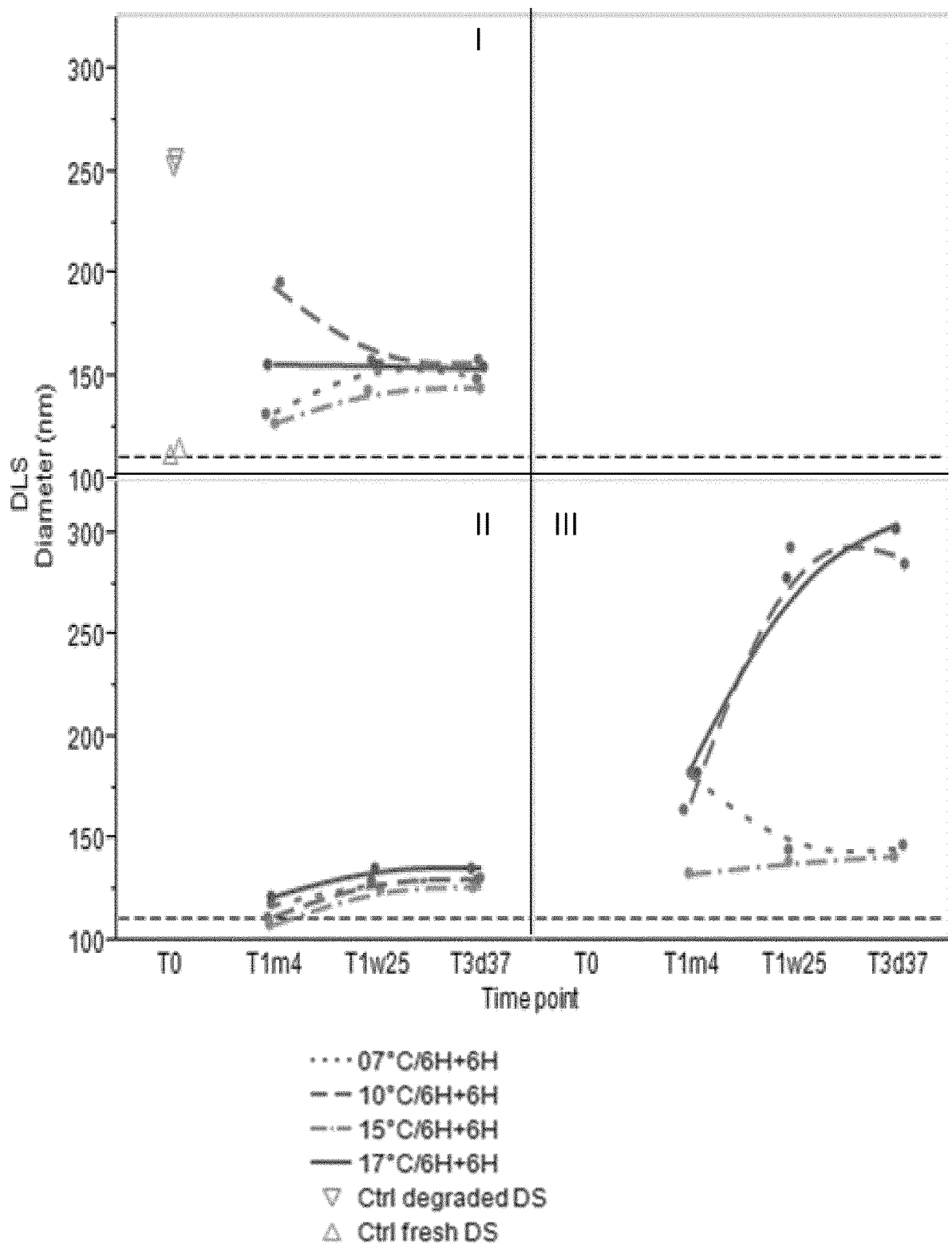
FIG. 3 illustrates the Dynamic Light Scattering (DLS) data as obtained in experiment 4: panel I—composition (a); panel II—composition (b); panel III: composition (c)

The results of the experiment are represented in FIG. 3.

Example 5

ChAd3Eboz was formulated using either (A) sucrose 8%, NaCl 25 mM, Tris 10 mM pH 7.4, histidine 10 mM, MgCl$_2$ 1 mM and polysorbate 80 0.02%, or, (B) trehalose 7%, sucrose 2% (residual), NaCl 6 mM, Tris 10 mM pH 7.4, histidine 10 mM, MgCl2 1 mM and polysorbate 80 0.02%. The freeze-drying cycle with annealing step as described for example 1 was applied to obtain the freeze-dried samples. The following rehydration media were tested:
After storage of the dried composition for 1 month at 4° C. (T1m4): NaCl 150 mM, NaCl 30 mM, and water for injection.

(WFI<NaCl 30 mM<NaCl 150 mM). In addition, trehalose-based formulation (A) provided better capsid stability compared to sucrose-based formulation (B) when using low-salt rehydration media (WFI and NaCl 30 mM).

As shown in the graph of FIG. 4.II (timepoint T2m4° C.), comparable results to WFI were obtained with salt-free rehydration media (sucrose 9.25% w/v and trehalose 9.25% w/v) with lyo samples stored for 2 months at 4° C. Also, again trehalose-based formulation (A) provided better capsid stability compared to sucrose-based formulation (B) when using low-salt rehydration media (WFI, trehalose 9.25% w/v and sucrose 9.25% w/v).

Example 6

The purpose of this experiment was to evaluate the feasibility of freeze-drying a ChAd155 vector under the same conditions as described in the preceding examples for ChAd3 vector hereinabove. The ChAd155 vector used in the experiment encodes an respiratory syncytial viral protein and is described in PCT/EP2016/063297.
Conditions evaluated were:
The freeze-drying cycle applied in example 1 (see FIG. 1, hereinafter referred to as cycle I) is compared to a freeze-drying cycle including the same sequence as in FIG. 1 but with an annealing step at −10° C. and a secondary drying just raised to 10° C. over 6 hours and stopped at this moment (see FIG. 5, hereinafter referred to as cycle II).
The impact of trehalose and histidine content was also assessed by comparing four compositions:
Composition (a): ChAd155 $1 \cdot 10^{11}$ pU/ml, Tris 10 mM pH 8.5, polysorbate 80 0.02%, MgCl$_2$ 1 mM, trehalose 9%, NaCl 8 mM, sucrose 2.5%, histidine 10 mM
Composition (b): ChAd155 $1 \cdot 10^{11}$ pU/ml, Tris 10 mM pH 8.5, polysorbate 80 0.02%, MgCl$_2$ 1 mM, trehalose 9%, NaCl 8 mM, sucrose 2.5%

Composition (c): ChAd155 1·10$^{11}$ pU/ml, Tris 10 mM pH 8.5, polysorbate 80 0.02%, MgCl$_2$ 1 mM, trehalose 7%, NaCl 6 mM (residual), sucrose 2.5%, histidine 10 mM Composition (d): ChAd155 1·10$^{11}$ pU/ml, Tris 10 mM pH 8.5, polysorbate 80 0.02%, MgCl$_2$ 1 mM, trehalose 7%, NaCl 6 mM (residual), sucrose 2.5%

Freeze-dried products are reconstituted with water for injection.

Two samples of bulk ChAd155, both before and after treatment for 30 min at 60° C., were used as positive and negative controls respectively.

Capsid disruption upon reconstitution of the dried composition was assessed using Quant-iT™ PicoGreen® assay (an ultra-sensitive fluorescent nucleic acid for quantifying double stranded DNA in solution) and infectivity (measuring the infectivity of the adenoviral particles by flow cytometric detection of cells stained for adenovirus hexon capsid protein).

The results of this experiment are presented in the table below (cf. graph of FIGS. 5 and 6):

| Cycle | Composition | PicoGreen® (ng/ml) (average values) | PicoGreen® normalized - ADN free (%) (average values) | Infectivity Hexon (% hexon) (average values) | Infectivity Hexon normalized (%) (average values) |
|---|---|---|---|---|---|
| I | a | 283.9 | 36.8 | 27.2 | 48.4 |
|  | b | 335.7 | 43.7 | 21.2 | 37.2 |
|  | c | 434.9 | 56.9 | 14.6 | 25.0 |
|  | d | 467.3 | 61.2 | 13.8 | 23.4 |
| II | a | 468.2 | 61.3 | 11.8 | 19.6 |
|  | b | 461.3 | 60.4 | 12.9 | 21.7 |
|  | c | 498.8 | 65.4 | 11.1 | 18.3 |
|  | d | 477.4 | 62.5 | 9.2 | 14.8 |
| Ctrl adenoviral stock | | 7.9 | 0.0 | 54.8 | 100.0 |
| Ctrl adenoviral stock degraded 30' at 60° C. | | 758.8 | 100.0 | 1.3 | 0.0 |

Example 7

This experiment aimed to confirm the protective impact of the annealing step on product integrity and to assess the impact of desorption kinetic processed during secondary drying.

The freeze-drying cycle selected in example 6 (see FIG. 5) was used to evaluate an annealing step of tray 3 hours and desorption kinetic until 12 hours by adding a secondary drying tray 6 hours. The evaluation was made based on composition (a) of example 6: ChAd155 1·10$^{11}$ pU/ml, Tris 10 mM pH 8.5, polysorbate 80 0.02%, MgCl$_2$ 1 mM, trehalose 9%, NaCl 8 mM, sucrose 2.5%, histidine 10 mM.

Freeze-dried products were reconstituted with water for injection.

Two samples of bulk ChAd155, both before and after treatment for 30 min at 60° C., were used as positive and negative controls respectively.

Capsid disruption upon reconstitution of the dried composition was assessed using Quant-iT™ PicoGreen® assay (an ultra-sensitive fluorescent nucleic acid for quantifying double stranded DNA in solution) and the viral infectivity by CCID50 (quantification of virus required to kill 50% of infected hosts or to produce a cytopathic effect (CPE) in 50% of inoculated cell culture).

Figure 5:
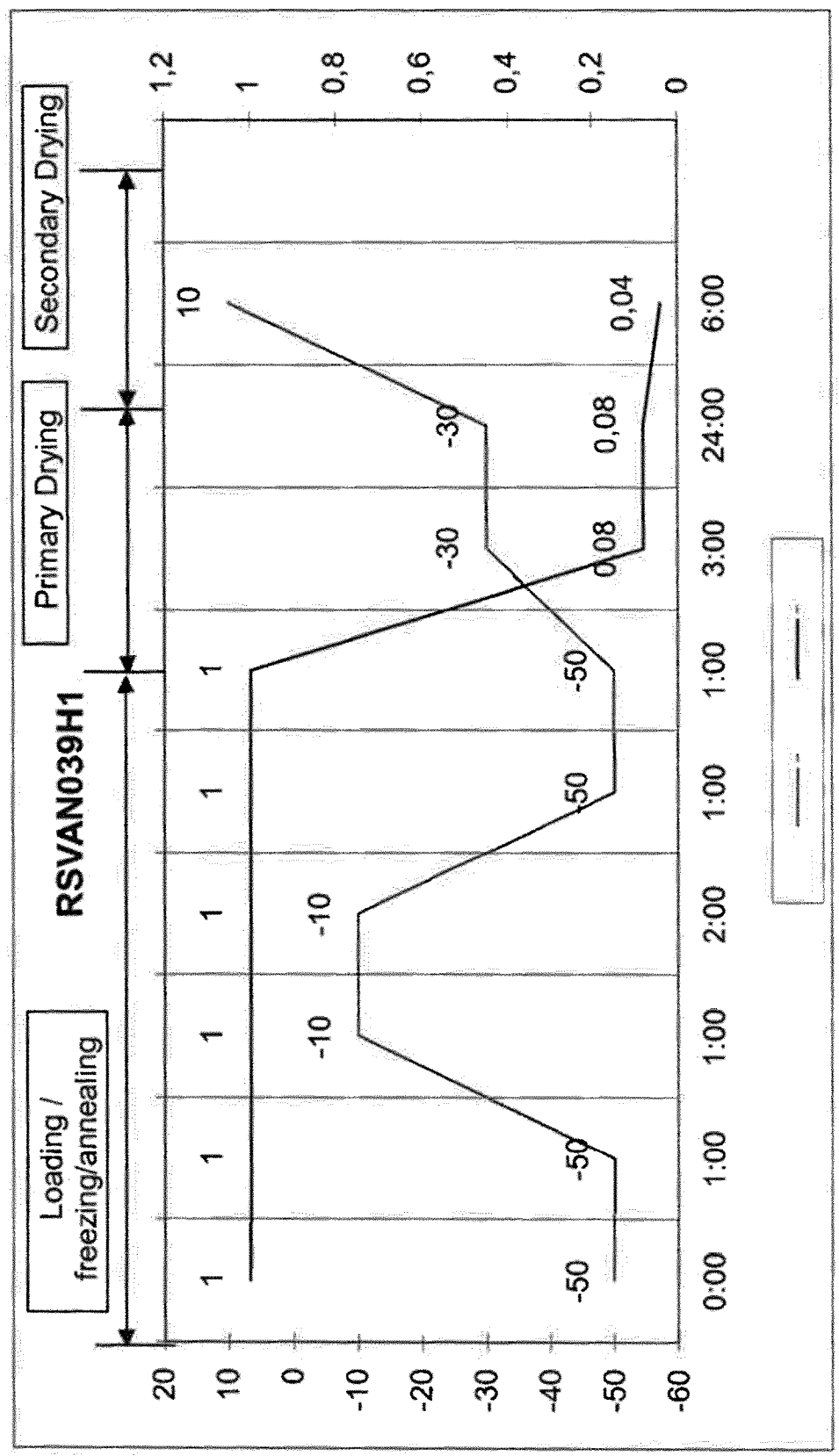
FIG. 5 illustrates the freeze drying cycle used in example 6.
Figure 6:
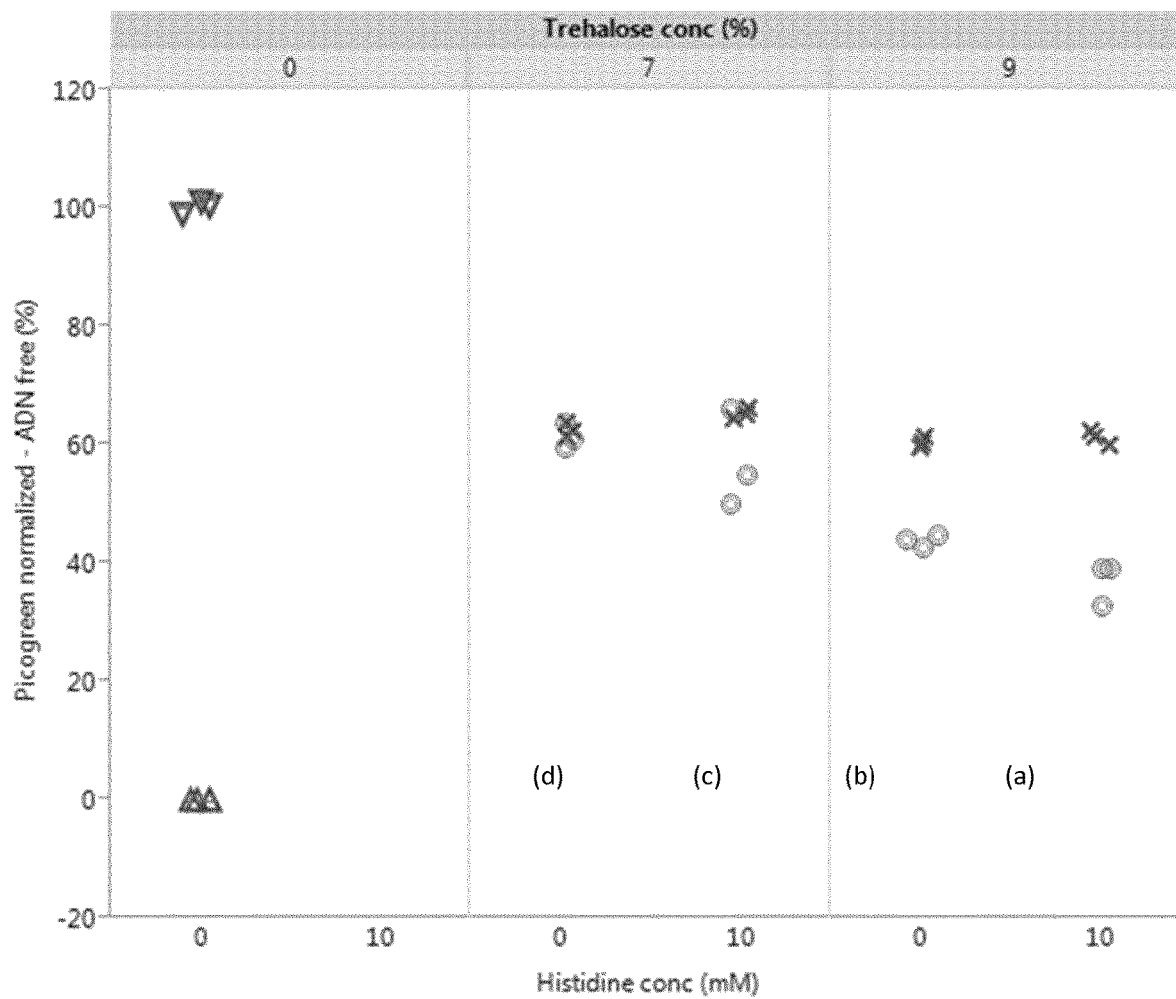
FIG. 6 illustrates the PicoGreen® data as obtained in experiment 6: Δ—control adenoviral stock, ∇—negative control degraded adenoviral stock, x—data obtained with samples obtained by freeze drying cycle I, ○—data obtained with samples obtained by freeze drying cycle II
Figure 7:
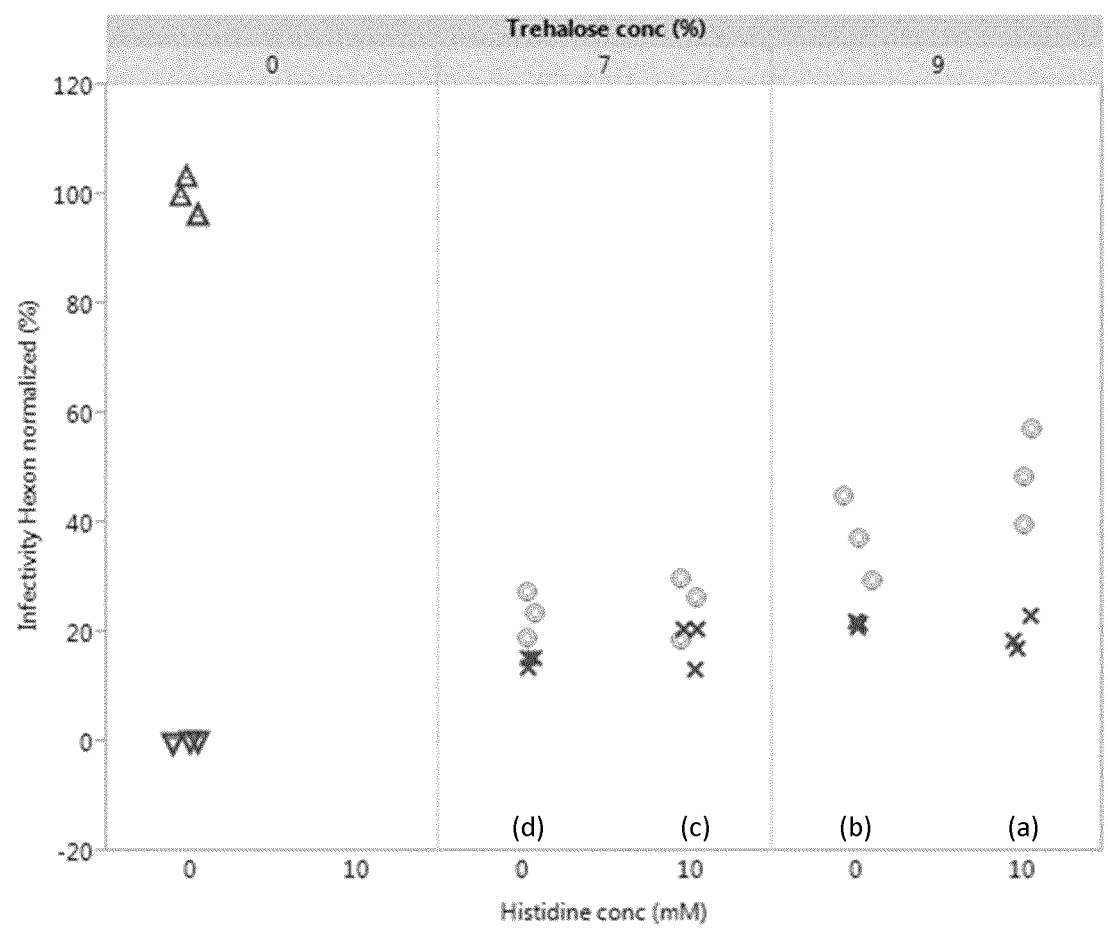
FIG. 7 illustrates Infectivity data as obtained in example 6: Δ—control adenoviral stock, ∇—negative control degraded adenoviral stock, x—data obtained with samples obtained by freeze drying cycle I, ○—data obtained with samples obtained by freeze drying cycle II
Figure 8:
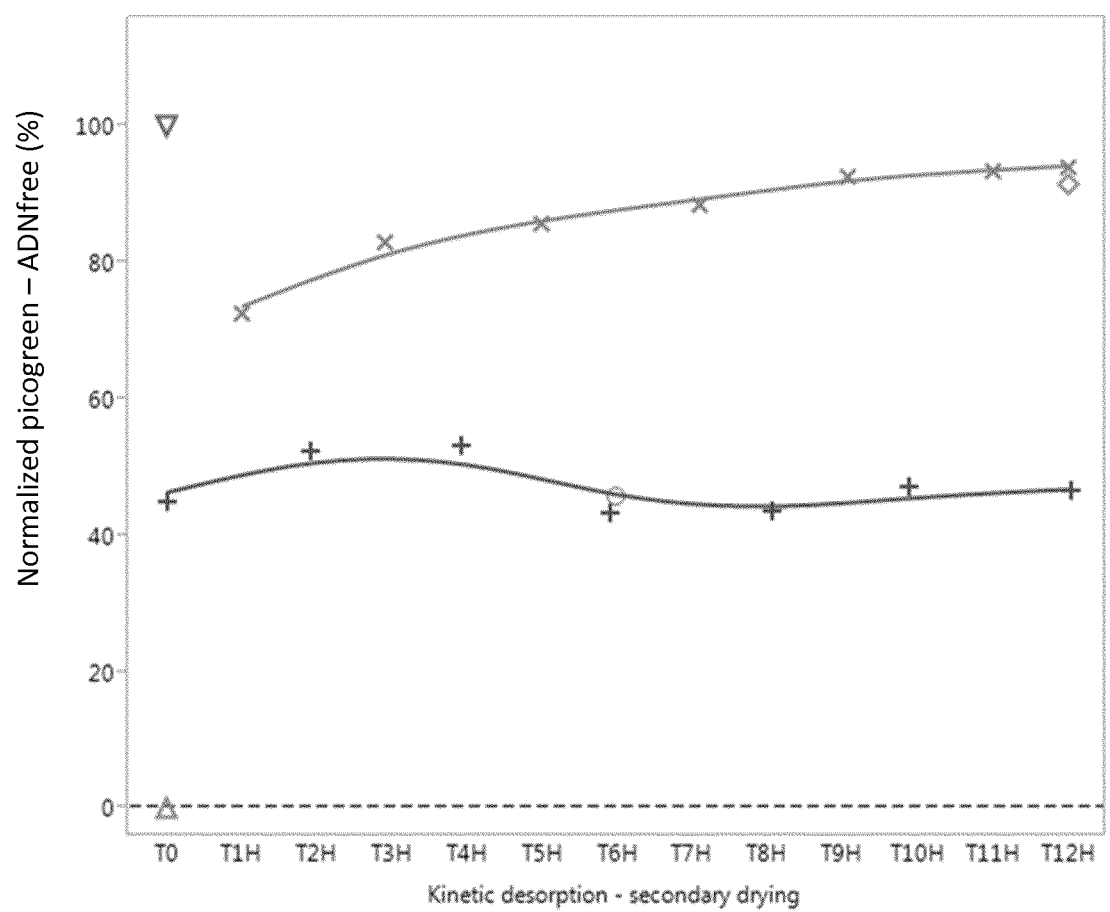
FIG. 8 illustrates PicoGreen® data and FIG. 9 illustrated Infectivity data as obtained in experiment 7: Δ—control adenoviral stock, ∇—negative control degraded adenoviral stock, +—data obtained using freeze drying cycle having sequence Freezing −52° C. with Annealing −10° C. (3 hours)/Primary drying −30° C./Secondary drying +10° C. (6H+6H), x—data obtained using freeze drying cycle having sequence Freezing −52° C. without Annealing/Primary drying −30° C./Secondary drying +10° C. (6H+6H), ◊—data obtained using freeze drying cycle having sequence slow Freezing at 0.5° C./min without annealing/Primary drying −30° C./Secondary drying +10° C. (6H+6H), ○—data obtained using freeze drying cycle having sequence Freezing −52° C. with Annealing −10° C. (2 hours)/Primary drying −30° C./Secondary drying +10° C. (6H+6H)
Figure 9:
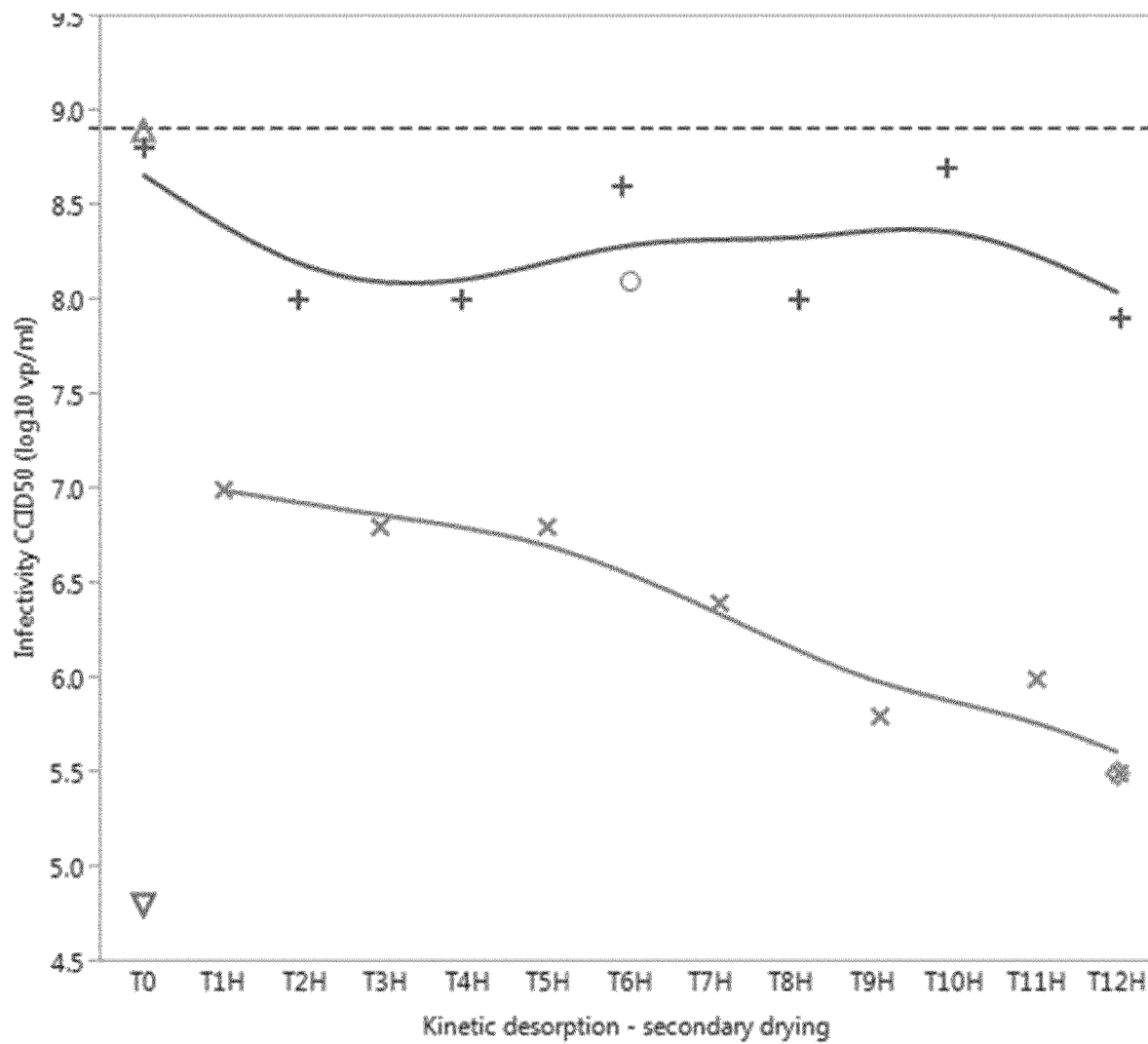

The results of this experiment are presented in the table below and illustrated in FIGS. 8 and 9:

| Annealing condition | Kinetic desorption - secondary drying | Picogreen (ng/ml) | Picogreen normalized - ADN free (%) | Infectivity CCID50 (log10 vp/ml) |
|---|---|---|---|---|
| −10° C./3 H | T0 | 280.5 | 44.9 | 8.8 |
|  | T2 H | 325.8 | 52.2 | 8.0 |
|  | T4 H | 330.8 | 53.0 | 8.0 |
|  | T6 H | 270.1 | 43.2 | 8.6 |
|  | T8 H | 271.0 | 43.4 | 8.0 |
|  | T10 H | 293.5 | 47.0 | 8.7 |
|  | T12 H | 290.8 | 46.6 | 7.9 |
| Without annealing | T1 H | 454.0 | 72.7 | 7.0 |
|  | T3 H | 518.3 | 83.0 | 6.8 |
|  | T5 H | 536.5 | 85.9 | 6.8 |
|  | T7 H | 552.7 | 88.5 | 6.4 |
|  | T9 H | 577.9 | 92.5 | 5.8 |
|  | T11 H | 584.4 | 93.6 | 6.0 |
|  | T12 H | 587.8 | 94.0 | 5.5 |
| Slow freezing: 0.5° C./min - no annealing - secondary drying +10° C./6 H + 6 H | | 571.7 | 91.5 | 5.5 |
| FIG. 5 condition: Annealing −10° C./2 H - secondary drying +10° C./6 H | | 285.3 | 45.7 | 8.1 |
| Ctrl adenoviral stock | | 0.0 | 0.0 | 8.9 |
| Ctrl adenoviral stock degraded 30' at 60° C. | | 624.6 | 100.0 | 4.8 |

What is claimed is:

1. A method of producing a simian adenoviral vector encoding an immunogenic transgene by
   (a) providing an aqueous mixture comprising a simian adenoviral vector in an amount of about $10^9$ to about $10^{12}$ viral particles per milliliter, sucrose in an amount of about 8% (w/v), sodium chloride in an amount of about 25 mM, a surfactant selected from poloxamer 188 and polysorbate 80 in an amount of about 0.02% (w/v), magnesium chloride in an amount of about 1.0 mM, histidine in an amount of about 10 mM, and Tris in an amount of about 10 mM wherein the pH is between about 7 and about 8; and
   (b) freezing the aqueous mixture by
      (1) reducing the temperature to below Tg' of the mixture for a minimum of about one hour;
      (2) applying an annealing step to the frozen mixture by elevating the temperature to a temperature above Tg' and below the melting temperature of the frozen mixture, without melting the frozen mixture;
      (3) maintaining the annealing temperature for about two hours, and
      (4) reducing the temperature over the course of about one hour to below the glass transition temperature in the frozen state (Tg');
   (c) drying the frozen mixture under reduced pressure while raising the temperature to about 17°; and
   (d) reconstituting the dried mixture in water.

2. The method according to claim 1, wherein in step a), the aqueous mixture is provided at a temperature between +2° and +8° C.

3. The method according to claim 1 wherein in step (b) (1) the temperature is reduced by applying a shelf temperature at least 10°.

4. The method according to claim 1 wherein in step (b) (1) the temperature is reduced at a rate of 2 to 10° C./min.

5. The method according to claim 1 wherein the infectivity of the reconstituted adenoviral vector, is about 45%, and wherein the infectivity of the reconstituted adenoviral vector from step (d) is assessed by comparing the transgene expression of the vector of step (d) to the transgene expression of the vector of step (a).

6. A method of producing a simian adenoviral vector encoding an immunogenic transgene by
   (a) providing an aqueous mixture comprising a simian adenoviral vector in an amount of about $10^9$ to $10^{12}$ viral particles per milliliter, sodium chloride in an amount of about 8 mM, sucrose in an amount of about 2.5%, trehalose in an amount of about 9%, a surfactant selected from poloxamer 188 and polysorbate 80 in an amount of about (w/v), magnesium chloride in an amount of about 1.0 mM, histidine in an amount of about 10 mM and Tris in an amount of about 10 mM, wherein the pH is between about 8 and about 9; and
   (b) freezing the aqueous mixture by
      (1) freezing the aqueous mixture by reducing the temperature to below Tg' of the mixture;
      (2) applying an annealing step to the frozen mixture by elevating the temperature without melting the frozen mixture over the course of about three hours and
      (3) reducing the temperature again to below the glass transition temperature in the frozen state (Tg');
   (c) drying the frozen mixture under reduced pressure for about six hours; and
   (d) reconstituting the dried mixture in water.

7. The method of claim 6, wherein the infectivity, of the reconstituted vector is about 50% to about 55%, and wherein the infectivity of the reconstituted adenoviral vector from step (d) is assessed by comparing the $CCID_{50}$ of the vector of step (d) to the $CCID_{50}$ of the vector of step (a).

* * * * *

UNITED STATES PATENT AND TRADEMARK OFFICE
CERTIFICATE OF CORRECTION

PATENT NO. : 10,722,470 B2
APPLICATION NO. : 15/746473
DATED : July 28, 2020
INVENTOR(S) : Erwan Bourles et al.

It is certified that error appears in the above-identified patent and that said Letters Patent is hereby corrected as shown below:

On the Title Page

Item (71), Applicant:
Change: "GLAXOSMITHKLINE BIOLOGICALS, SA, Rixensart (BE)"
To: --GLAXOSMITHKLINE BIOLOGICALS SA, Rixensart (BE)--

In the Claims

Column 22, Line 15, Claim 6:
Change: "amount of about (w/v), magnesium chloride in an"
To: --amount of about 0.02% (w/v), magnesium chloride in an--

Signed and Sealed this
Fourteenth Day of June, 2022

*Katherine Kelly Vidal*

Katherine Kelly Vidal
*Director of the United States Patent and Trademark Office*